US012711623B2

(12) United States Patent
Kheradvar et al.

(10) Patent No.: US 12,711,623 B2
(45) Date of Patent: Aug. 18, 2026

(54) CHARACTERIZATION OF THREE-DIMENSIONAL INCOMPRESSIBLE FLOWS USING ECHO PARTICLE IMAGE VELOCIMETRY

(71) Applicant: THE REGENTS OF THE UNIVERSITY OF CALIFORNIA, Oakland, CA (US)

(72) Inventors: Arash Kheradvar, Irvine, CA (US); Gianni Pedrizzetti, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 369 days.

(21) Appl. No.: 18/351,084

(22) Filed: Jul. 12, 2023

(65) Prior Publication Data

US 2024/0020841 A1 Jan. 18, 2024

Related U.S. Application Data

(60) Provisional application No. 63/368,219, filed on Jul. 12, 2022.

(51) Int. Cl.
*A61B 8/00* (2006.01)
*A61B 8/06* (2006.01)
(Continued)

(52) U.S. Cl.
CPC .............. *G06T 7/0014* (2013.01); *A61B 8/06* (2013.01); *A61B 8/0883* (2013.01); *A61B 8/481* (2013.01); *A61B 8/483* (2013.01); *G06T 5/50* (2013.01); *G06T 7/246* (2017.01); *G16H 30/40* (2018.01); *G06T 2200/04* (2013.01); *G06T 2207/10132* (2013.01); *G06T 2207/20212* (2013.01); *G06T 2207/30048* (2013.01); *G06T 2207/30104* (2013.01)

(58) Field of Classification Search
None
See application file for complete search history.

(56) References Cited

U.S. PATENT DOCUMENTS 5,912,815 A * 6/1999 Kim ........................ G06T 7/262 700/32
10,716,519 B2 * 7/2020 del Alamo de Pedro .................. A61B 8/0883

(Continued)

*Primary Examiner* — Dov Popovici
(74) *Attorney, Agent, or Firm* — Ashurst Perkins Coie US LLP; Babak Tehranchi; Gautam Thatte

(57) ABSTRACT

Systems and methods for producing velocity data associated with three-dimensional (3D) flow field images. In some embodiments, the method includes receiving data associated with a plurality of frames of a flow field relating to image data acquired by a medical imaging device, in which the data includes information corresponding to measurements of the flow field over time within a chamber; performing, for each of the plurality of frames, the following operations including: generating, for a respective frame, a data correction based on an interaction of the flow field with the chamber, applying the data correction to a velocity field corresponding to the respective frame, and imposing an incompressibility constraint for the flow field on one or more data points of the respective frame; and generating, subsequent to imposing the incompressibility constraint, a plurality of corrected velocity fields each of which corresponds to one of the plurality of frames.

18 Claims, 14 Drawing Sheets

200A

Receiving, at one or more processors, data associated with a plurality of frames of a flow field relating to image data acquired by a medical imaging device, the data including information corresponding to measurements of the flow field over time within a chamber
202

Performing, using the one or more processors, for each of the plurality of frames, the following operations including Generating, for each of the plurality of frames, a data correction based on an interaction of the flow field with the chamber, applying the data correction to a velocity field corresponding to the respective frame, and imposing an incompressibility constraint for the flow field on one or more data points of the respective frame
204

Generating, using the one or more processors, subsequent to imposing the incompressibility constraint, a plurality of corrected velocity fields each of which corresponds to one of the plurality of frames
206

(51) Int. Cl.

| | |
|---|---|
| ***A61B 8/08*** | (2006.01) |
| ***G06T 5/50*** | (2006.01) |
| ***G06T 7/00*** | (2017.01) |
| ***G06T 7/246*** | (2017.01) |
| ***G16H 30/40*** | (2018.01) |

(56) References Cited

U.S. PATENT DOCUMENTS

2014/0149055 A1* 5/2014 Falahatpisheh ...... A61B 8/5223 702/45
2021/0012887 A1* 1/2021 Maessen ................ G16H 50/50

* cited by examiner

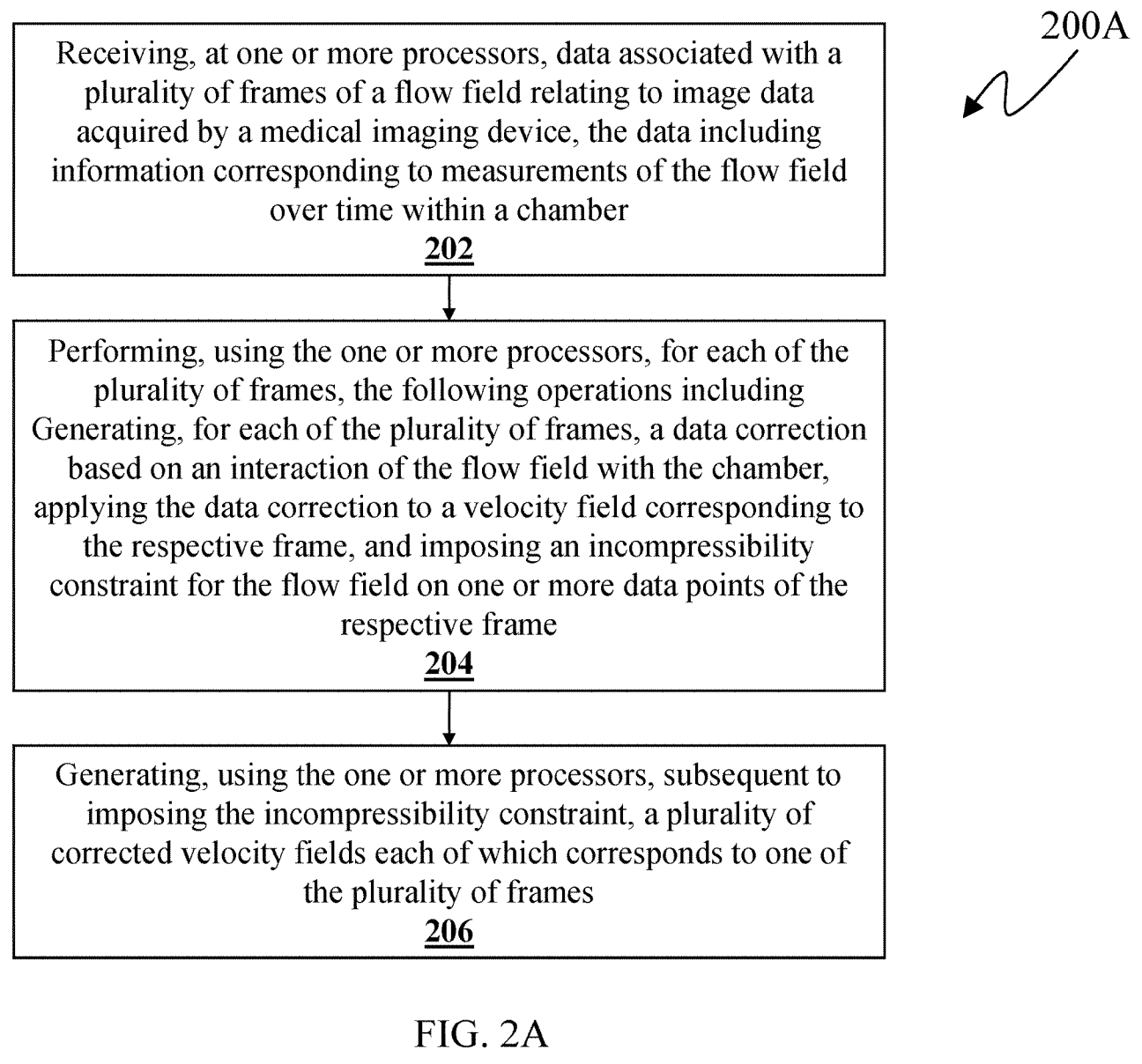

200A

Receiving, at one or more processors, data associated with a plurality of frames of a flow field relating to image data acquired by a medical imaging device, the data including information corresponding to measurements of the flow field over time within a chamber
202

Performing, using the one or more processors, for each of the plurality of frames, the following operations including Generating, for each of the plurality of frames, a data correction based on an interaction of the flow field with the chamber, applying the data correction to a velocity field corresponding to the respective frame, and imposing an incompressibility constraint for the flow field on one or more data points of the respective frame
204

Generating, using the one or more processors, subsequent to imposing the incompressibility constraint, a plurality of corrected velocity fields each of which corresponds to one of the plurality of frames
206

FIG. 2A

Control Subject (C)

(D)

KE<mJ/mL>
0.04
0.03
0.02
0.01
0

(E)

Dissipation
rate mW/mL
5.000e-03
3.750e-03
2.500e-03
1.250e-03
0.000e+00

FIG. 10

CHARACTERIZATION OF THREE-DIMENSIONAL INCOMPRESSIBLE FLOWS USING ECHO PARTICLE IMAGE VELOCIMETRY

CROSS-REFERENCE TO RELATED APPLICATIONS

This patent document claims priority to and benefits of U.S. Provisional Patent Application No. 63/368,219 entitled "CHARACTERIZATION OF THREE-DIMENSIONAL INCOMPRESSIBLE FLOWS USING ECHO PARTICLE IMAGE VELOCIMETRY" filed on Jul. 12, 2022. The entire content of the aforementioned patent application is incorporated by reference as part of the disclosure of this patent document.

STATEMENT REGARDING FEDERALLY SPONSORED RESEARCH OR DEVELOPMENT

This technology was made with government support under grant no. 5R01HL153724-02 awarded by the National Institutes of Health (NIH). The government has certain rights in the technology.

TECHNICAL FIELD

This patent document relates to systems, devices and techniques for hemodynamics, and in particular quantitative analysis of intracardiac blood flow based on real-time echocardiography.

BACKGROUND

Blood flow pattern is the fingerprint of cardiac performance. Each heart disease has unique blood flow characteristics and a variation in the blood flow pattern may indicate a change in the overall cardiac performance. Existing echocardiography implementations often use two-dimensional (2D) blood flow information to quantify cardiac dysfunction.

SUMMARY

The technology disclosed in this document can be implemented to provide methods, systems, and devices for monitoring a three-dimensional incompressible flow using echo particle image velocimetry. Embodiments of the present technology include receiving, at one or more processors, data associated with a plurality of frames of a flow field relating to image data acquired by a medical imaging device, the data including information corresponding to measurements of the flow field over time within a chamber; performing, using the one or more processors, for each of the plurality of frames, operations including: generating, for a respective frame, a data correction based on an interaction of the flow field with the chamber, applying the data correction to a velocity field corresponding to the respective frame, and imposing an incompressibility constraint for the flow field on one or more data points of the respective frame; and generating, using the one or more processors, subsequent to imposing the incompressibility constraint, a plurality of corrected velocity fields each of which corresponds to one of the plurality of frames. In some embodiments, the technology further includes monitoring, using the one or more processors, an intra-cycle variation of a parameter of the flow field based on the plurality of corrected velocity fields, in which the intra-cycle variation of the parameter may relate to a pathological condition.

BRIEF DESCRIPTION OF DRAWINGS

FIG. 2A illustrates a flowchart of an example method for producing velocity data associated with three-dimensional (3D) flow field images according to embodiments of the present technology.

DETAILED DESCRIPTION

Echocardiographic particle image velocimetry (echo-PIV) is a non-invasive ultrasonic technique for finding the multi-component velocity vectors in opaque flows. It is based on particle image velocimetry (PIV), a technique used for characterizing flow fields. A contrast agent, e.g., particles that may be used as flow tracers for such purposes include microbubbles filled with octafluoropropane encapsulated in either a lipid or a protein outer shell.

In existing implementations, the echo-PIV is an integral part of echocardiography, which is routinely used in the diagnosis, management, and follow-up of patients with any suspected or known heart diseases. An echocardiography is typically performed by placing a transducer on various locations on the patient's chest and upper abdomen and directed toward the heart, releasing high-frequency sound waves, picking up echoes of the sound waves, transmitting them as electrical impulses, and converting the electrical impulses into images of the heart. It is one of the most widely used diagnostic imaging modalities in cardiology. It can provide a wealth of helpful information, including the size and shape of the heart (internal chamber size quantification), pumping capacity, and the location and extent of any tissue damage, assessment of valves and cardiac masses. An echocardiogram can also give physicians other estimates of heart function, such as a calculation of the cardiac output, ejection fraction, and diastolic function (how well the heart relaxes).

However, the efficacy of the echo-PIV can be limited in scenarios with higher flow velocities. The echo-PIV data is generated by typically tracking flow particles on a frame-by-frame basis, i.e., tracking a particular particle of the flow from one frame to the next frame; thus, if the frame rate of the echo-PIV is too low with respect to the velocity of the flow, then the resulting echo-PIV images may have limited efficacy. For example, existing implementations of the echo-PIV are unable to produce reliable images when the velocity of the flow is greater than meters/sec.

Moreover, existing echocardiography implementations that use two-dimensional (2D) blood flow information to quantify cardiac dysfunction, while useful, may lack sufficient accuracy for characterizing complex three-dimensional flows, such as the flows in hearts with congenital defects or in pulmonary hypertension. However, the quantification of three-dimensional (3D) cardiac flow patterns has remained a challenging fluid dynamics problem and modern echocardiography-based velocimetry techniques cannot yet acquire data with sufficient spatial and temporal resolutions to improve clinical diagnosis. With existing systems, this is believed to be partly due to the limited frame rate of 3D echocardiographic acquisitions, a limitation imposed by the speed of the ultrasound wave in the tissue.

Figure 1:
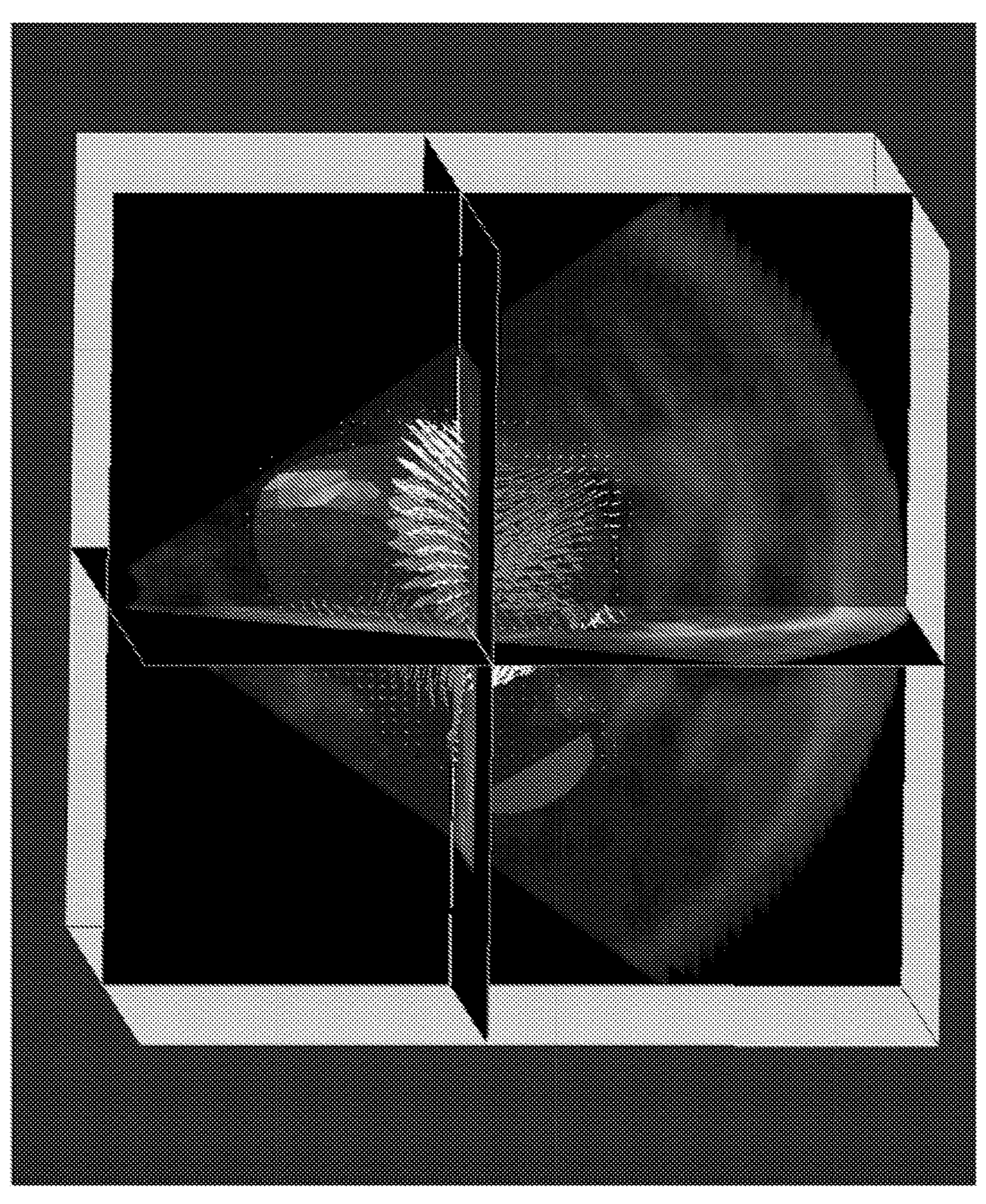
FIG. 1 illustrates an example of a boundary flow velocity that is determined using embodiments of the disclosed technology.

Embodiments of the disclosed technology cure this and other deficiencies of the existing echo-PIV-based systems by implementing one or more complementary techniques to improve the echo-PIV images that include: acquiring high frame rate (~100 frames per second (fps) and higher) data in the presence of a contrast agent by focusing on a region of interest, and/or improving quantitative analysis based on the images (or image data) so acquired by (a) imposing boundary or border conditions associated with the chamber where the flow is occurring, (b) using a two-dimensional perpendicular flow, and/or (c) accounting for the Doppler effects of the flow. In addition, incompressibility constraints are imposed on each pixel of the frame to produce improved images. The improved image of the flow in the chamber, an example of which is illustrated in FIG. 1, can be used with greater confidence in subsequent diagnostic tests.

For illustration purposes, various embodiments of the present technology are described with reference to the application of assessing right ventricular (RV) state of energy based on ultrasound imaging. It is understood that it is not intended to limit the scope of the present technology and that the present technology is suitable in other applications involving image-based characterization or quantitative analysis of incompressible flows. In this example use case, RV state of energy includes RV flow kinetic energy and RV myocardial work that reflect both right heart pressure and RV flow kinematics. Abnormal vortex formation can disturb RV fluid dynamics leading to an increase in energy dissipation. This increase in energy dissipation can reduce right heart efficiency, taking additional RV compensation to maintain the stroke volume. As this vicious cycle continues, RV dilatation and loss of contractility can appear, which can be reflected in the RV state of energy. In this connection, embodiments of the present technology relate to various improvements involving volumetric echocardiographic particle image velocimetry (V-Echo-PIV) and quantitative analysis based thereon.

Some embodiments of the present technology provide improved flow visualization by acquiring high frame rate (~100 frames per second (fps) and higher) data in the presence of a contrast agent. According to some embodiments, an ultrasound system can acquire B-mode images of the RV and a 3D flow by tracing individual bubbles in consecutive frames. Apical long axis RV focused view can be used for full-volume acquisition by limiting the sector width and imaging depth solely to the entire RV from tricuspid valve to the apex. In some embodiments, left ventricular opacification (LVO) setting for ultrasonic enhancing agents (UEA) is avoided, thereby mitigating or avoiding its negative effects on frame rates. Visualization of the 3D RV flow and border/wall dynamics can be achieved by IV administration of a contrast agent (e.g., Optison™) and normal saline (NS). Dynamic 4D border detection and analysis may be performed based on the high frame rate data so acquired. The high frame rate data acquisition allows 4D echocardiography including determination and/or analysis of intra-cycle flow information (including, e.g., time-dependent instabilities in the flow), compared to cardiac MRI which allows visualization of intra-cardiac flow but not intra-cycle information due to the phase-average performed therein.

Additionally or alternatively, some embodiments of the present technology improve the accuracy of velocimetry techniques, e.g., V-Echo-PIV, by improving the quantitative analysis on the image data acquired according to embodiments of the present technology. The improvements include imposing the chamber's boundary dynamics to the flow velocity field that is determined. For example, the velocity of the flow at the inlets and outlets of the chamber is determined by imposing the conservation of mass principle as the rate of volumetric changes per area of the inlet or outlet.

Accordingly, in some embodiments, sequential B-mode brightness fields are processed by an optical flow technique based on the conservation of brightness in all voxels, from which a three-dimensional (3D) velocity field of the blood flow at various instants of a single cardiac cycle may be determined according to the temporal variation of the brightness field. Such 3D velocity field having intra-cycle temporal resolution may allow the determination of evolving vortex flows in the RV, which is three-dimensional and cannot be visualized with existing echocardiography. In addition, the 3D velocity field having intra-cycle temporal resolution may allow the determination of the kinetic energy and dissipation rate by considering the rate of deformation of the blood flow due to shear forces within the RV.

FIG. 2A illustrates a flowchart of an example method for producing velocity data associated with three-dimensional (3D) flow field images according to embodiments of the present technology. The process 200A may include at 202 receiving, at one or more processors, data associated with a plurality of frames of a flow field relating to image data acquired by a medical imaging device. The data may include information corresponding to measurements of the flow field over time within a chamber. In some embodiments, the chamber is a heart chamber. The chamber may undergo a cyclic motion such as cardiac motion. The medical imaging device may be configured to acquire image data of the chamber and a flow in the chamber. Examples of the medical imaging device include an ultrasound device, a magnetic resonance imaging (MRI) device, or the like, or a combination thereof. Merely by way of example, the medical imaging device is an ultrasound device, and image data is generated using a transducer (e.g., a matrix probe) operably coupled to the medical imaging device.

In some embodiments, a portion of the image data that relates to a frame of the plurality of frames include a representation limited to the chamber. For example, for scanning the chamber, the scan area may be set or adjusted by specifying one or more scanning parameters including, e.g., a sector size (e.g., a sector width), an imaging depth, or the like, or a combination thereof. The data associated with the plurality of frames may be determined by stitching information acquired in multiple cycles of the cyclic motion of the chamber. In some embodiments, a contrast agent may be applied to a patient before the image data is acquired as described elsewhere in the present disclosure. Merely by way of example, the data received at 202 may include high frame-rate 4D echocardiographic data (~100 fps) from an RV flow may be acquired in the presence of a contrast agent (e.g., Optison™).

In some embodiments, the medical imaging device may acquire the image data by exporting high frame rate VolDICOMS using a software configured to retrieve, visualize, manage, and/or export ultrasound images (e.g., 3D ultrasound images). An example of a suitable software include Qlab provided by PHILIPS™. Qlab is provided here as an example for illustration purposes and not intended to be limiting. The medical imaging device (or another component of the system described herein) may perform dynamic border extraction on the images using, e.g., software configured to allow delineating a 3D border surrounding the flow region of interest. The software may be configured to provide a graphical user interface (GUI) for visualizing such a border, reviewing it, and correcting it if needed. Examples of such software include Tomtec 4D RV function when the region of interest is the RV, or Tomtec 4D LV analysis when the region is the left ventricle. In some embodiments, the dynamic border extraction can be performed manually via an appropriate graphical user interface (GUI) or by an automated procedure that may also allow correcting borders (e.g., via a GUI in 3D shape or on 2D cross sections of custom RV views). The correction may be performed manually or facilitated by automatic procedures.

The process 200A at 204 may include performing operations for processing the data associated with the plurality of frames. The process 200A includes, for each of the plurality of frames, generating, a data correction based on an interaction of the flow field with the chamber, applying the data correction to a velocity field corresponding to the respective frame, and imposing an incompressibility constraint for the flow field on one or more data points of the respective frame. The data correction may be determined by one or more of: (a) the interaction of the flow field with one or more boundaries of the chamber (e.g., see also 220 in FIG. 2B), (b) a two-dimensional perpendicular flow field data within the chamber (e.g., see also 222 in FIG. 2B), and/or (c) a Doppler effect of the flow within the chamber (e.g., see also 224 in FIG. 2B). Description regarding the incompressibility constraint for the flow field may be found elsewhere in the present disclosure. See, e.g., 230 in FIG. 2B.

The process 200A at 206 may include generating, using the one or more processors, subsequent to imposing the incompressibility constraint, a plurality of corrected velocity fields each of which corresponds to one of the plurality of frames. The corrected velocity fields may be stored in an electronic file on a storage device, and/or processed further to elucidate information relating to the flow in the chamber being imaged, or a condition relating to the flow (e.g., a pathological condition of a patient whose heart, or a portion thereof (e.g., RV), is imaged.

Figure 2B:
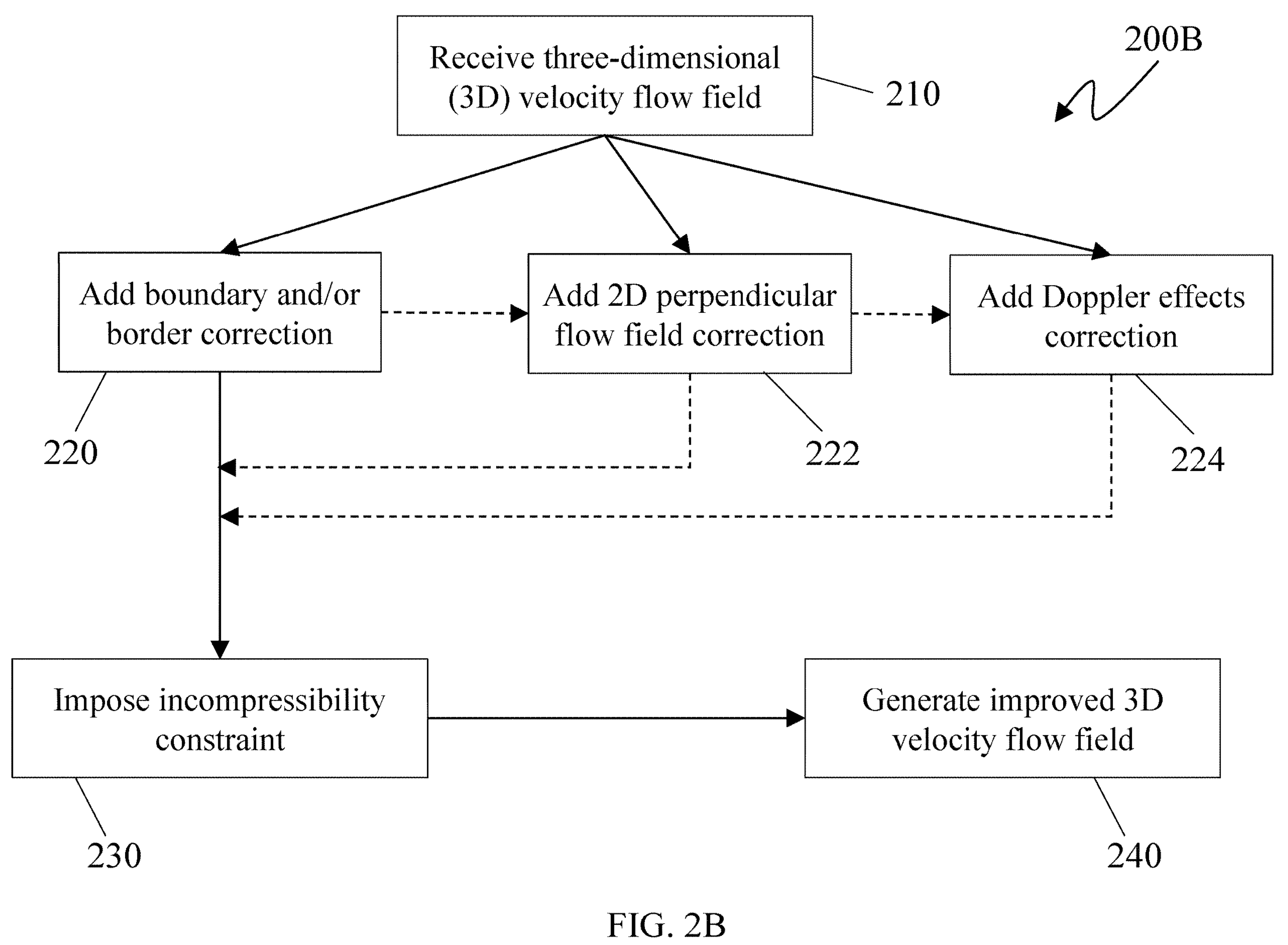
FIG. 2B illustrates a flowchart of an example method for improving the visualization of an echo-PIV image, according to embodiments of the disclosed technology.

FIG. 2B illustrates a flowchart of an example process for improving the visualization of a three-dimensional (3D) flow field. The process 200B may include receiving, at one or more processors, data associated with a plurality of frames relating to image data acquired by a medical imaging device, similar to 202 as illustrated in FIG. 2A. The data may include information corresponding to measurements of a flow field within a chamber that undergoes a cyclic motion. For example, as illustrated in FIG. 2B, the process 200B begins, in step 210, with receiving the data associated with the plurality of frames that includes 3D velocity flow field of a flow within a chamber. In some embodiments, the 3D velocity flow field may be echo-PIV flow field data. In some embodiments, the received 3D velocity flow field may have been generated using particle image velocimetry, particle tracking methods, phase contrast magnetic resonance imaging (MRI), e.g., 4D flow MRI, ultrasound velocimetry, and/or multi-angular Doppler techniques.

In some embodiments, the medical imaging device may include an ultrasound scanner. For example, the chamber is a heart chamber such as a right ventricle. The cyclic motion of the chamber is a cardiac motion that proceeds according to a sinus rhythm. The medical imaging device is a cardiac ultrasound device or scanner configured to perform echocardiography. The image data may be acquired using a matrix probe. To allow a high temporal resolution of the data associated with the plurality of frames, and results determined based thereon, a high frame rate may be achieved by way of at least one of (a) limiting the scan area, or (b) by stitching information acquired in multiple cycles of the cyclic motion of the chamber. Merely by way of example, according to some embodiments, high frame-rate 4D echocardiographic data (~100 fps) from an RV flow may be acquired in the presence of a contrast agent (e.g., Optison™).

The scan area may be limited and/or adjusted by specifying one or more scanning parameters including, e.g., a sector size (e.g., sector width) and/or an imaging depth. The scanning parameters may be selected based on a region of interest (e.g., RV). For example, the method includes acquiring B-mode images of the RV from apical long axis RV focused view for full-volume acquisition by limiting the sector size (e.g., sector width) and/or imaging depth solely to the entire RV from tricuspid valve to the apex. For patients of various sizes, the scanning parameters may be adjusted accordingly. For example, the scanning parameters may be adjusted based on a patient's age, size, etc. Merely by way of example, by limiting the scan area to RV only, an average frame rate may be increased from about 8 Hz to about 30 Hz or above.

Additionally or alternatively, information acquired in multiple cycles of the cyclic motion of the chamber may be stitched to improve the frame rate. For example, an average frame rate may be increased from about 30 Hz to about 100 Hz or above by stitching information acquired in 4 heart beats. The stitching may be performed based on motion phase information of the cyclic motion. Merely by way of example, such information in the cardiac motion may be embedded in the sinus rhythm.

A contrast agent may be used in the RV imaging to enhance the visualization of blood flow and improving the imaging of the heart. Examples of the contrast agent suitable for echocardiography include Definity (Perflutren Lipid Microsphere), Optison (Perflutren Protein-Type A Microspheres), Sonovue (Sulfur Hexafluoride Microbubbles), or the like, or a combination thereof. The contrast agent may be administered to a patient by intravenous (IV) injection. Although the administration of contrast may cause a negative effect the frame rates given that temporal resolution is sacrificed for spatial resolution, the negative effect may be mitigated or compensated by the one or more measures (e.g., limiting scanning area, stitching information from multiple cycles of the cyclic motion) configured to improve the frame rate as described elsewhere in the present disclosure. LVO setting for ultrasonic enhancing agents (UEA) may be avoided, thereby mitigating or avoiding its negative effects on frame rates.

The contrast agent may include bubbles, and once in the bloodstream, travel through the heart chambers and blood vessels. When ultrasound waves are directed towards the heart, the bubbles present in the bloodstream act as highly reflective surfaces for the ultrasound waves and create strong echoes when they interact with the ultrasound waves. This enhanced reflection allows the ultrasound machine to produce clearer and more detailed images of the heart chambers, valves, and blood flow. Merely by way of example, the blood flow (e.g., a 3D velocity field of the blood flow) in the RV may be visualized or determined by tracing individual bubbles in consecutive frames.

Figure 3:
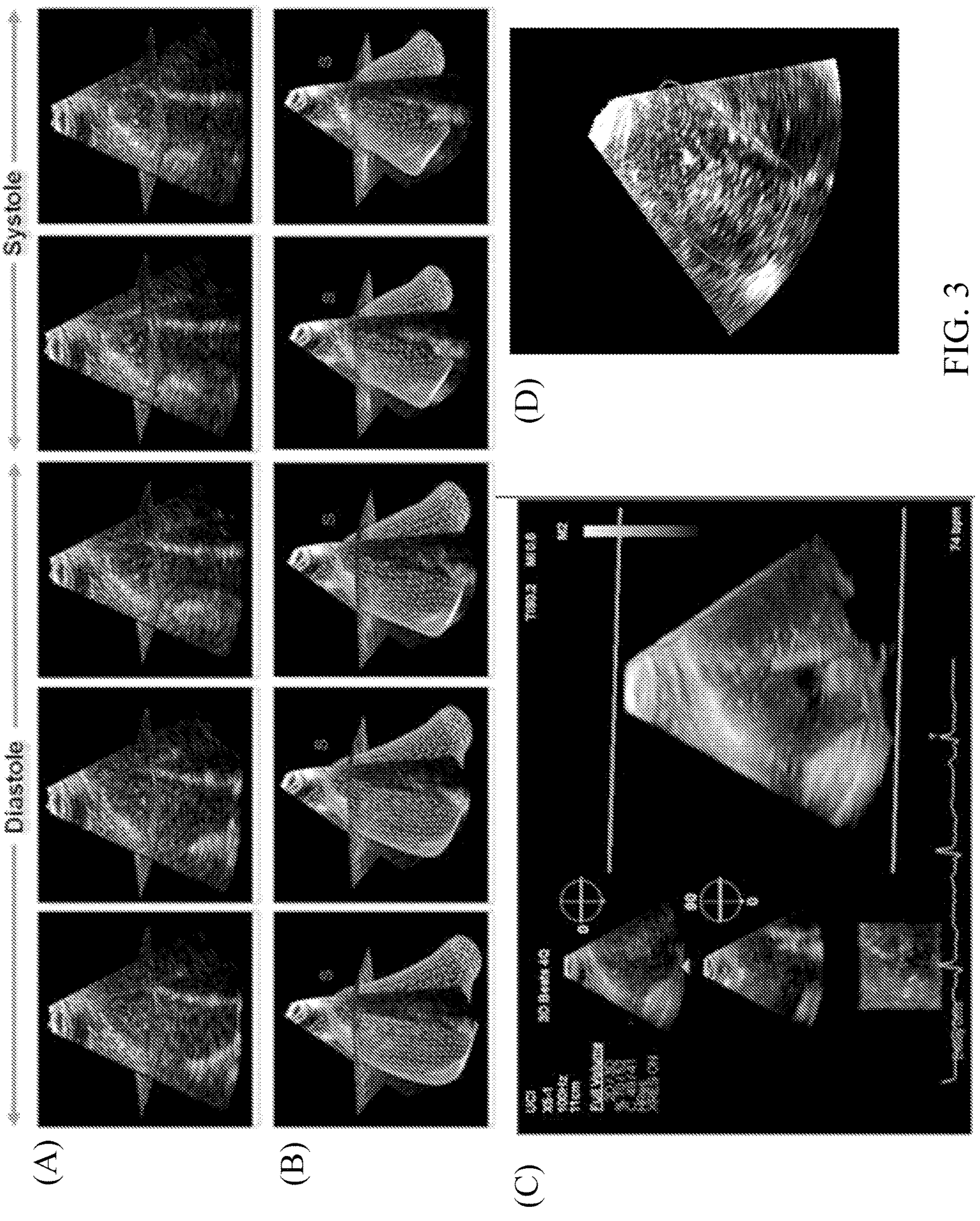
FIG. 3 illustrates images acquired in example implementations of 4D echocardiography according to embodiments of the present disclosure.

FIG. 3 illustrates images acquired in example implementations of 4D echocardiography according to embodiments of the present disclosure. The images were acquired using X5_1c matrix probe on the ultrasound system EPIQ CV9 by PHILLIPS™ for a full volume, RV focused, apical view scan at 100 Hz acquisition frame rate by stitching 4 cycles according to embodiments of the present disclosure. The blood flow was seeded via IV administration of Optison™ contrast at a 2:20 to 2:40 ratio of Contrast/Normal Saline resulted in visible bubble movements 50-500 bubble density. A desired contrast density for an IV bolus injection was achieved at the contrast/NS ratio of 2:18 followed by a 1 to 2 mL of NS flush. Recordings of image data started when flow motion was visible (e.g., about 4-6 seconds after injection). A mechanical index (MI) set in the range of 0.4 to 0.6 for Optison™ offered the best results among the images acquired. The reproducibility of the current method was tested via processing two separate acquisitions of the same subject. Cartesian 4D Brightness fields as illustrated in (A) and (C) of FIG. 3 were exported using Qlab. Dynamic border extraction was performed using TomTec 4d RV function by manually correcting borders of custom RV views as illustrated in (B) of FIG. 3. FIG. 3 demonstrates successful acquisition of 3D echocardiographic images at 100 Hz that images contrast bubbles (see the portion within the contour in (D) of FIG. 3) in a cine of image frames to acquire the RV blood flow dynamics by means of echocardiographic particle image velocimetry (Echo-PIV), and accordingly the RV state of energy. This approach can also be used for other cases of complex anatomy and hemodynamics (e.g., congenital heart defects and valvular heart disease).

The process 200B continues by generating, for each of the plurality of frames, a data correction based on an interaction of the flow fields with one or more boundaries of the chamber. The data correction may be generated based on one or more of: (a) the interaction of the flow field with one or more boundaries of the chamber as illustrated in 220, (b) a two-dimensional perpendicular flow field data within the chamber as illustrated in 222, and/or (c) a Doppler effect of the flow within the chamber as illustrated in 224.

As illustrated in step 220, by adding, to the 3D velocity flow field data, a correction term based on the boundary or border conditions of the chamber. This correction term leverages the movement (or lack of movement) of the chamber boundary to account for changes in the flow velocity and directions and assumes that the velocity of the flow particles at the boundary will match the velocity of the boundary itself. For example, if the 3D velocity flow field is the blood in the right ventricle of the heart (e.g., as illustrated in FIG. 1), and the right ventricle is known to be stationary in a particular frame, then the velocity of the flow particle touching the inner surface of the right ventricle will be zero. This correction term is computed for each frame of the input 3D velocity flow field and added to the velocity field data of the corresponding frame.

In some embodiments, the velocity estimated by echo-PIV can present inaccuracies near the boundaries. In particular, next to a solid (tissue) boundary, the fluid velocity must match that of the boundary itself; therefore, if a point at the boundary is described by a material three-dimensional position vector X(t) that can change with time t, the fluid velocity, U, at that position is given by the time derivative of the position vector as $$U = \frac{dX}{dt}.$$

Differently, an open boundary is represented by the cross section of an open orifice (e.g., a valve position) where flow transits across. In this case, the total flow rate crossing the open boundary is dictated by the volumetric change of the chamber. If we call V(t) the chamber volume then the total flow rate, Q, is given by $$Q = \frac{dV}{dt}$$

such that the average, relative normal velocity across the valve is $$\frac{Q}{A}$$

where A(t) is the opening area of the cross section in time. Assuming that the velocity is predominantly perpendicular to the valve, directed with the normal unit vector n, the relative velocity at the open boundary can then be estimated as $$U = \frac{Q}{A}n.$$

Additionally, if the open boundary presents a non-negligible velocity, $$\frac{dX}{dt},$$

of its position X(t), the absolute fluid velocity can be obtained by properly subtracting such a boundary velocity from the relative velocity. Correcting the velocity at the open boundaries can be particularly relevant because velocities are highest therein and difficult to obtain accurately by echo-PIV.

In step 230, an incompressibility constraint (that assumes the flow is incompressible) is imposed on each pixel of every corrected (or improved) frame. In one example, the incompressibility constraint is implemented using the Poisson equation, and applying this constraint to each pixel of a frame serves to "align" the particles in the corresponding frame.

For instance, the first estimated velocity is given by echo-PIV and by the reliable values at the boundaries. Imposing the incompressibility constraint in accordance with the disclosed embodiments allows for the correction of the estimation and the propagation of the boundary values to the entire flow field. In some embodiments, the velocity before correction is considered as a tentative velocity field $U^*$ that is reliable in some positions, such as at the boundaries or in some other positions where measurements can be considered reliable and does not satisfy the mass conservation at all other positions. Based on this tentative velocity, a more reliable velocity field U that complies with the constraint of conservation of mass at every point in the fluid domain may be obtained. Conservation of mass, for an incompressible fluid, requires that the velocity field has zero divergence: $\nabla \cdot U=0$. This constraint can be employed once the corrected field is expressed as the sum of the initial (or tentative) field $U^*$ plus an irrotational correction that is expressed as the gradient of a scalar field, say $\varphi$, such that $U=U^*+\nabla\varphi$. The incompressibility constraint gives a Poisson equation for the correction $\nabla^2\varphi=-\nabla \cdot U^*$, where the second term is computed from the tentative field. The Poisson equation is a linear second order equation of the elliptic type that can be solved by many numerical methods (e.g., finite difference methods, gradient discretization methods, domain decomposition methods, etc.). Its solution, in this example embodiment, gives the scalar potential $\varphi$ from which the original velocity field can corrected for an improved velocity field.

In step 240, the improved 3D velocity flow field is generated. The improved data can be transmitted or stored for use in subsequent diagnostic tests or procedures.

As illustrated in FIG. 2B, the process 200B in some embodiments can, additionally or alternatively to step 220, include the incorporation of other correction terms, e.g., a correction term based on a two-dimensional perpendicular flow field in step 222 and/or a correction term based on the Doppler effects of the flow in step 224. The correction term based on the Doppler effects of the flow can be generated if the flow is moving in the direction of the transducer but is typically unreliable and not incorporated if the flow is moving transverse to the transducer.

In some embodiments, and as described above for the boundaries, the original velocity field can be corrected at any position of the 3D flow domain where reliable information is available. In an example, in the case that a more reliable measurement is provided on one or more subdomains (e.g., on one or more planes where a more accurate velocimetry is performed), then the velocity vectors on that plane are modified according to the given measurement. In another example, if the velocity component along a predefined direction is available (e.g., given by 2D or 3D Doppler echocardiography), the entire vector can be modified (typically enhanced) to match with the Doppler information. After the reliable velocities are embedded, the incompressibility condition is applied to all other positions to improve the velocity field.

In some embodiments, any combination of the steps 220, 222 and 224 can be performed. For example, only one of the correction terms may be applied to the input 3D velocity flow field to generate the improved 3D velocity flow field. In other embodiments, any two of the correction terms may be generated and added to the input 3D velocity flow field. In yet other embodiments, all three correction terms can be added to the input 3D velocity flow field. As illustrated in FIG. 2B, the incompressibility constraint (in step 230) is imposed on the data points for each frame after the one or more corrections have been added to the 3D velocity flow field of the input frame. In some embodiments, the incompressibility constraint may be imposed based on a set of pixels (i.e., the velocity field data) for each frame or based on a frame-by-frame basis.

Figure 2C:
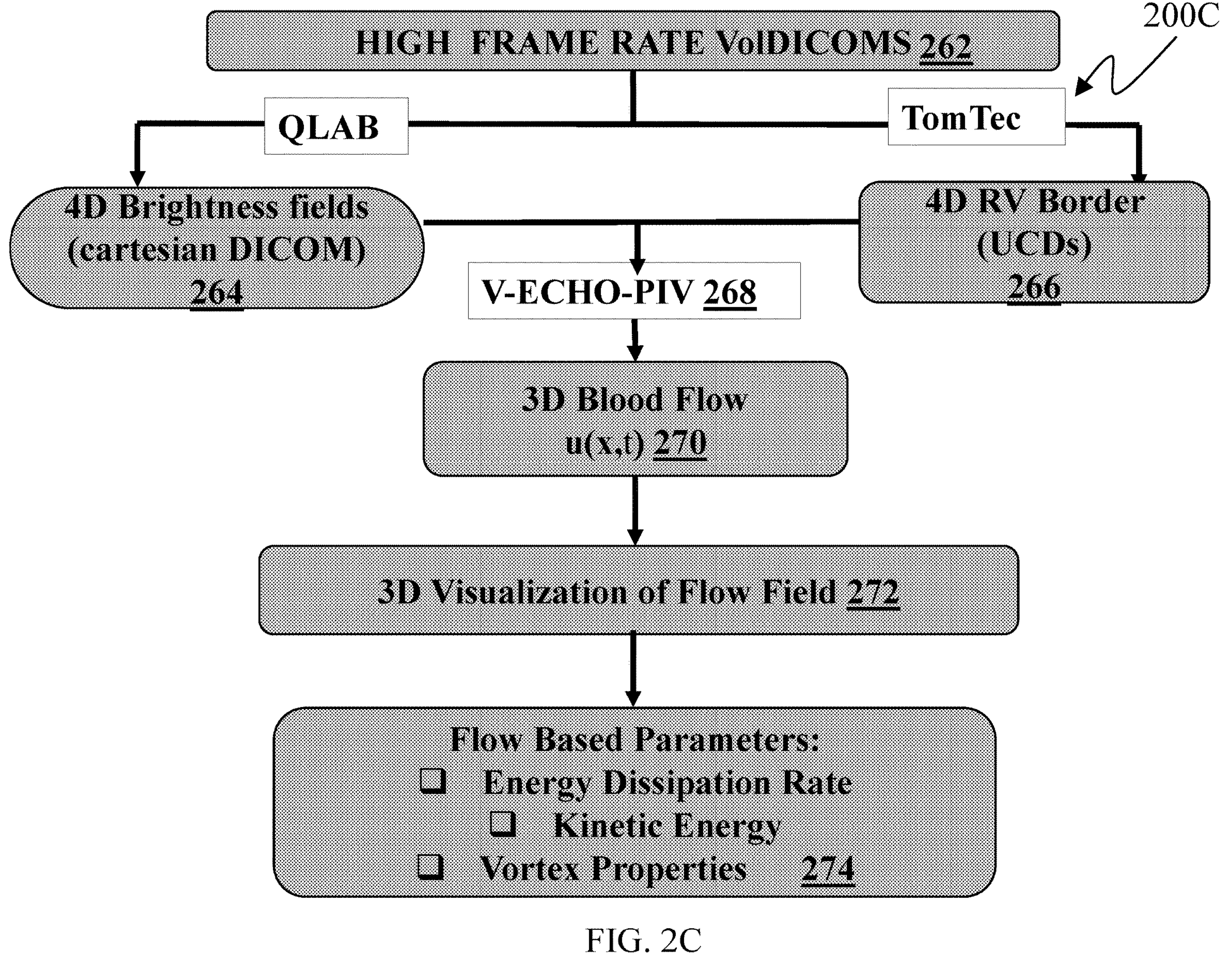
FIG. 2C illustrates a flowchart of an example method for producing velocity data associated with three-dimensional (3D) flow field images according to embodiments of the present technology.

FIG. 2C illustrates a flowchart of an example method for producing velocity data associated with three-dimensional (3D) flow field images according to embodiments of the present technology. The process 200C may include acquire high frame rate VolDICOMS at 262, similar to relevant operations in 202 and 210, which is not repeated here.

The process 200C may include at 264 exporting the high frame rate VolDICOMS using, e.g., Qlab. Qlab is provided here as an example for illustration purposes and not intended to be limiting. It is understood that other software configured to retrieve, visualize, manage, and/or export ultrasound images (e.g., 3D ultrasound images) may be used. The process 200C may include at 266 performing dynamic border extraction using, e.g., the TomTec 4d RV function. The TomTec 4d RV function is provided here as an example for illustration purposes and not intended to be limiting. It is understood that other software configured to allow delineating a 3D border surrounding the flow region of interest may be used. The software may be configured to provide a graphical user interface (GUI) for visualizing such a border, reviewing it, and correcting it if needed. Examples of such software include Tomtec 4D RV function when the region of interest is the RV, or Tomtec 4D LV analysis when the region is the left ventricle. In some embodiments, the dynamic border extraction can be made manually via an appropriate graphical user interface (GUI) or by an automated procedure that may also allow correcting borders (e.g., via a GUI in 3D shape or on 2D cross sections of custom RV views). The correction may be performed manually or facilitated by automatic procedures.

The process 200C may include performing V-Echo-PIV at 268 so that a velocity field of the 3D blood flow over time may be estimated at 270. The process 200C may further include determine a corrected velocity field, similar to that as described in 204 and 220-224, which is not repeated here. The process 200C may then generate, based on the velocity field (e.g., a corrected velocity field), 3D visualization of the flow field at 272. The process 200C may further determine, based on the velocity field (e.g., a corrected velocity field), flow based parameters at 274. Merely by way of example with reference to 4D echocardiography performed on the RV of a subject (e.g., a control subject, a patient), flow based parameters so determined may include energy dissipation rate, kinetic energy, vortex properties, or the like, or a combination thereof. As described elsewhere in the present disclosure, the flow based parameters may relate to or indicate a pathological condition (e.g., PH or other pathological condition) of the subject being imaged.

In some embodiments, the method as disclosed herein including, e.g., process 200A, process 200B, 200C, may continue by monitoring an intra-cycle variation of a parameter of the flow field based on the plurality of corrected velocity fields. The intra-cycle variation of the parameter may relate to a pathological condition. For example, the chamber is a right ventricle of a heart. The parameter of the flow field being monitored includes one or more of a vortex, a flow kinetic energy, or a dissipation rate per cardiac cycle. The method can predict whether the pathological condition exists based on the intra-cycle variation of the parameter. In some embodiments, the method includes comparing the intra-cycle variation of the parameter with a reference intra-cycle variation of the parameter; determining that a difference between the intra-cycle variation of the parameter with a reference intra-cycle variation of the parameter exceeds a threshold; and in response to determining that the difference between the intra-cycle variation of the parameter with a reference intra-cycle variation of the parameter exceeds a threshold, determining that the pathological condition exists.

Figure 4:
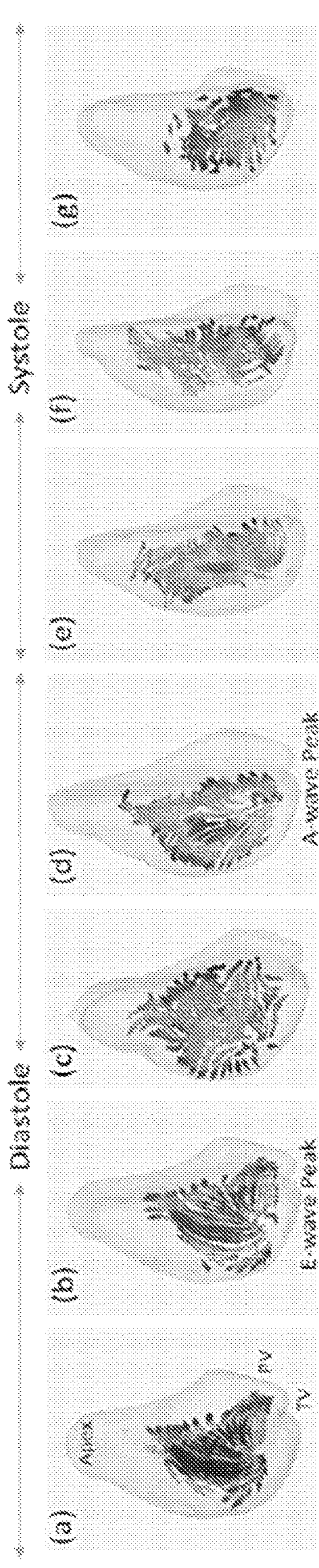
FIGS. 4 and 5 show the cine blood velocity in various phases throughout the cardiac cycle and iso-surfaces of transient tricuspid vortex during diastolic RV filling, respectively, in a healthy subject determined according to some embodiments of the present disclosure.
Figure 5:
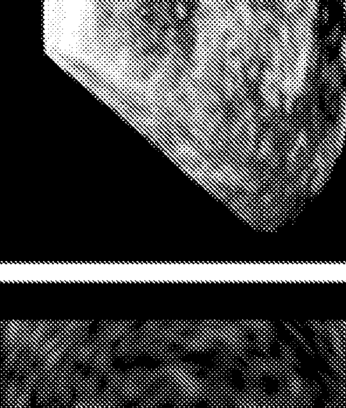
Figure 5:
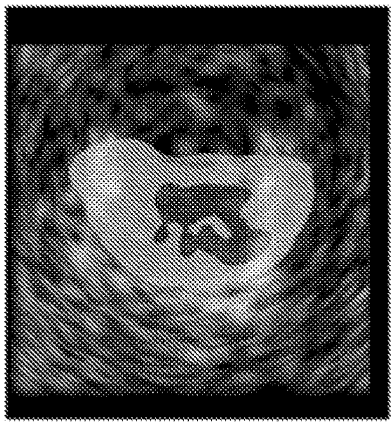
Figure 5:
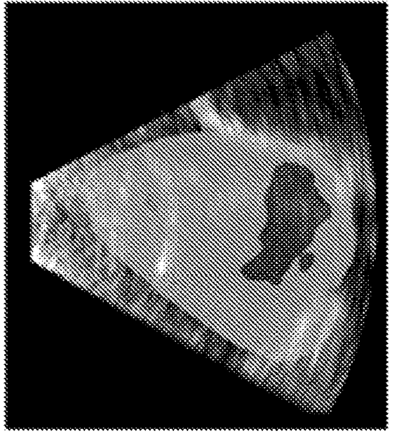
Figure 5:
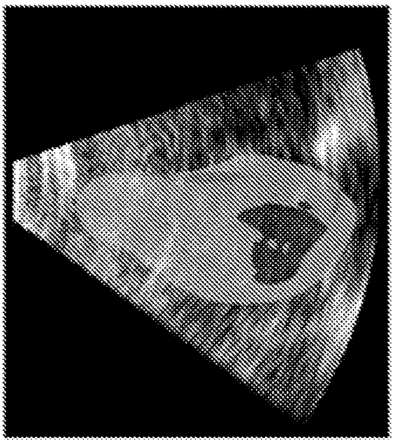

FIGS. 4 and 5 show the cine blood velocity in various phases throughout the cardiac cycle and iso-surfaces of transient tricuspid vortex during diastolic RV filling, respectively, in a healthy subject determined according to some embodiments of the present disclosure. The corresponding image data was acquired using a X5_1c matrix probe on the Phillips machine EPIQ CV9 for a full volume, RV focused, apical view scan at 100 Hz acquisition frame rate; the blood flow was seeded via IV administration of Optison™ contrast at a 2:16 (Optison/NS) ratio. VolDICOM datasets were processed with V-Echo-PIV to obtain RV blood flow velocity field during the full cardiac cycle. The results show that throughout a cardiac cycle, 4D flow inside the RV can be quantified and characterized with high temporal resolution using V-Echo-PIV. Specifically, FIG. 4 shows the cine blood velocity in the healthy subject with a 68 bpm heart rate in which V-Echo-PIV acquired 86 three-dimensional velocity vector fields in one cardiac cycle, given the setting of 100 Hz acquisition rate. FIG. 4 shows featured flow patterns at, e.g., peak E-wave (a), peak A-wave (d), as well as systolic flows (e-g). FIG. 5 illustrates the iso-surfaces of transient tricuspid vortex during diastolic RV filling. These results demonstrate that V-Echo-PIV is a real-time platform that acquires RV flow field at high temporal resolution without the need for phase-average. Therefore, it can be used as a viable alternative to 4D Flow MRI to visualize and evaluate real-time intra-cardiac blood flow, and for vortex imaging. V-Echo-PIV takes only a very short acquisition time (e.g., in the order of seconds the recording, or very few minutes when including preparation phases for image optimization and IV infusion) and can be used where an echocardiography machine with matrix probes is available.

Figure 6:
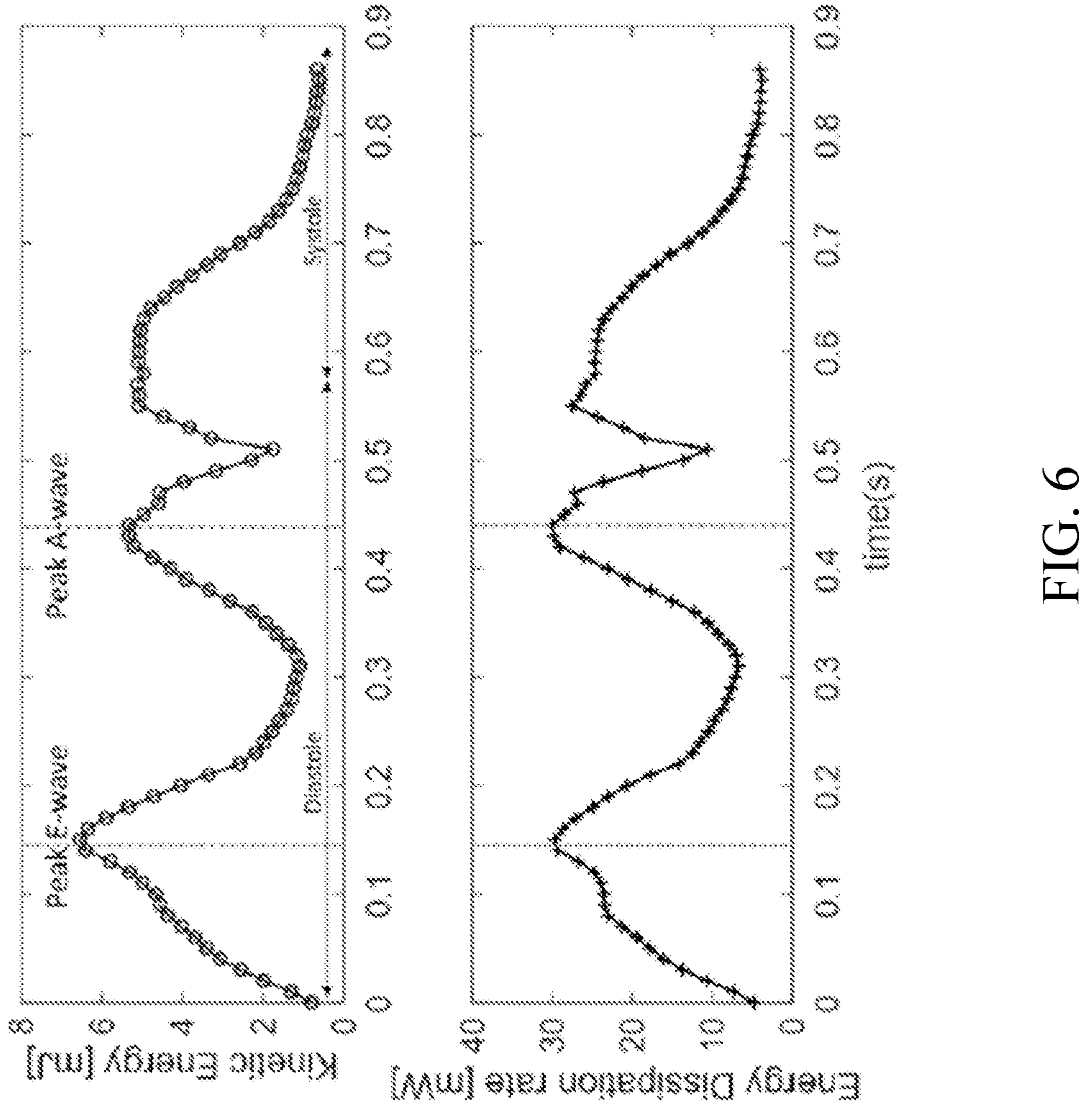
FIG. 6 shows a trend of total RV kinetic energy and dissipation rate per cardiac cycle determined according to some embodiments of the present disclosure.
Figure 7:
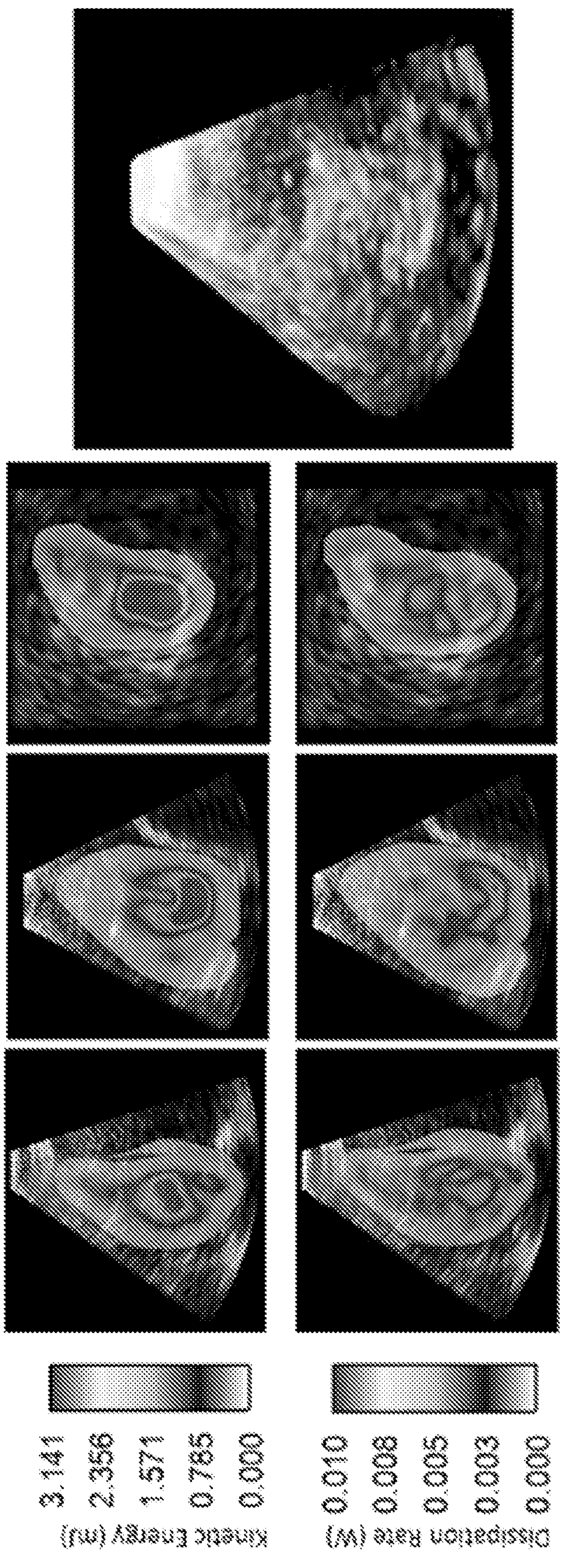
FIG. 7 shows the spatial map of the kinetic energy and dissipation rate during peak E-wave over the RV volume corresponding to the results illustrated in FIG. 6 determined according to some embodiments of the present disclosure.

FIG. 6 shows a trend of total RV kinetic energy and dissipation rate per cardiac cycle determined according to some embodiments of the present disclosure. The corresponding image data was acquired using Phillips EPIQ CV9 machine equipped with X5_1c matrix probe to acquire full volume, RV focused, apical view scans at 100 Hz. Blood flow is seeded via IV administration of Optison™ contrast at a 2:16 ratio. V-Echo-PIV processes the 4D echocardiography data to obtain the RV's 3D blood flow velocity field for each instant of cardiac cycle. The kinetic energy was calculated from velocity magnitude and dissipation rate was computed accordingly by considering the rate of deformation of blood flow due to shear forces within the RV. FIG. 6 shows the trend of the total RV kinetic energy and dissipation rate per cardiac cycle. As illustrated in FIG. 6, three extrema for both kinetic energy and dissipation rate were found at the peak E-wave, peak A-wave, and during early systole. FIG. 7 shows the spatial map of the kinetic energy and dissipation rate during peak E-wave over the RV volume corresponding to the results illustrated in FIG. 6. The results demonstrate the RV kinetic energy and dissipation rate determined from real-time 4D echocardiography using V-Echo-PIV technique. Given that the V-Echo-PIV does not involve phase-average as MRI, it can be used as a viable alternative to 4D Flow MRI to compute intra-cardiac blood flow energetics with a reasonable spatial and temporal resolution.

Figure 8:
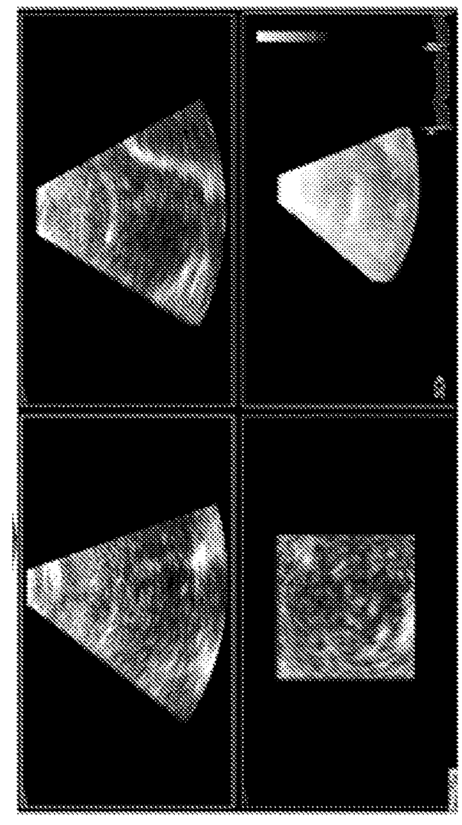
FIGS. 8-11 show results acquired from a pulmonary hypertension patient and a healthy control subject according to some embodiments of the present disclosure.
Figure 8:
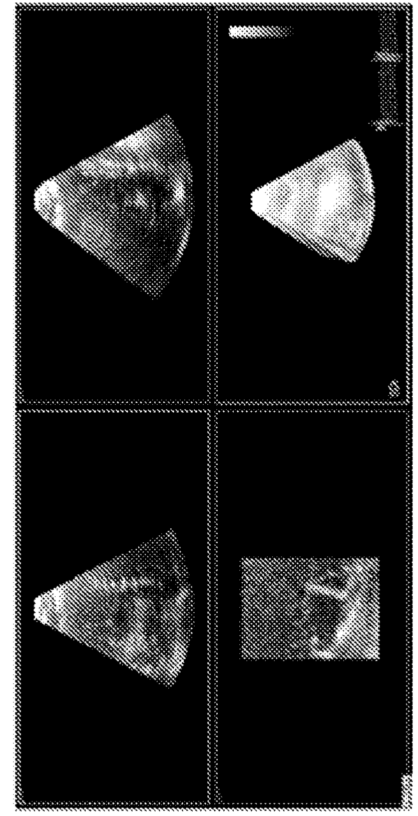
Figure 8:
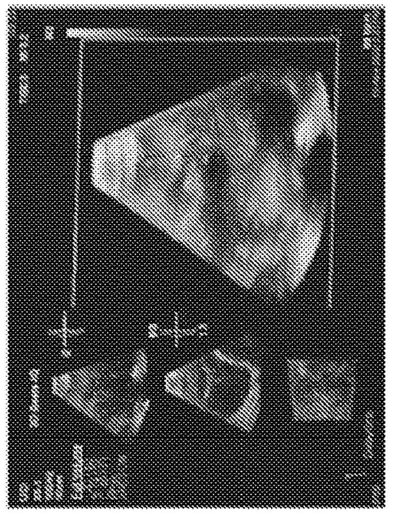
Figure 8:
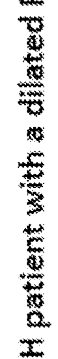
Figure 8:
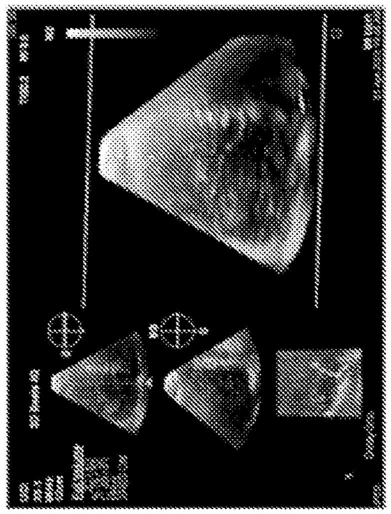
Figure 9:
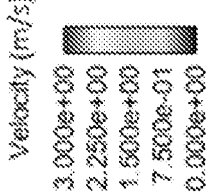
Figure 9:
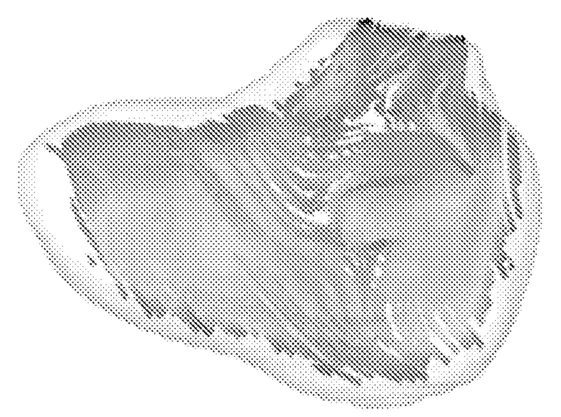
Figure 9:
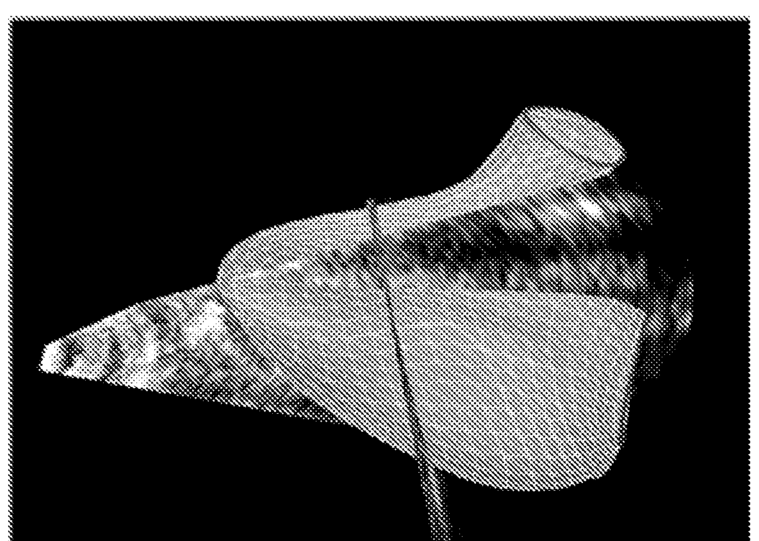
Figure 10:
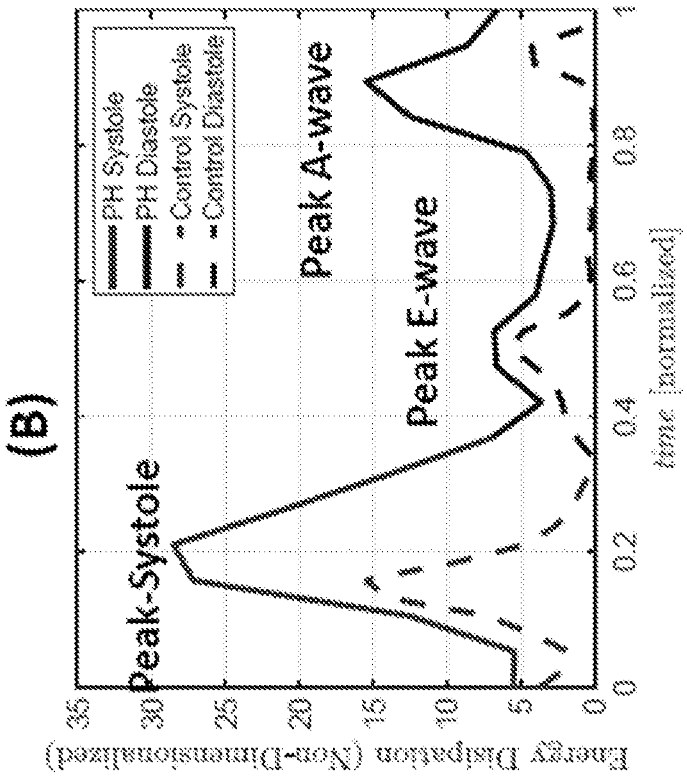
Figure 10:
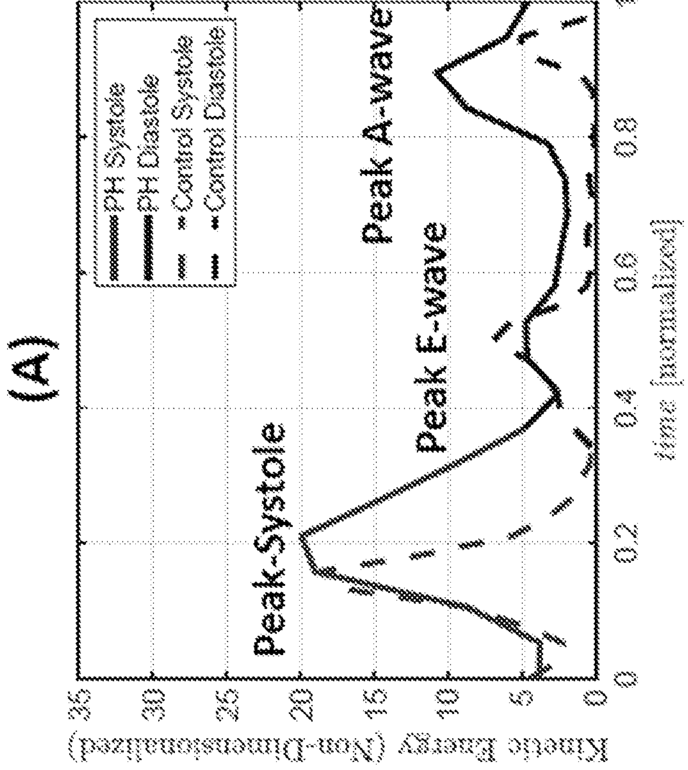
Figure 11:
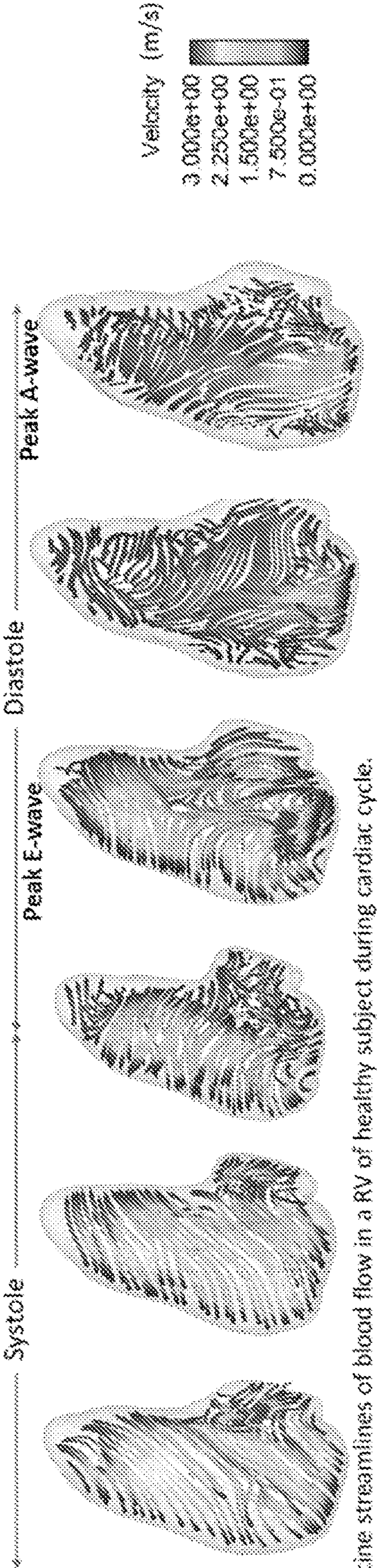

FIGS. 8-11 show results acquired from a pulmonary hypertension patient and a healthy control subject according to some embodiments of the present disclosure. FIG. 8 shows images acquired in example implementations of 4D echocardiography for a control subject and a pulmonary hypertension (PH) patient according to embodiments of the present disclosure. FIG. 9 illustrates 3D RV blood flow velocity fields characterized by V-Echo-PIV technique based on the image data of FIG. 8. FIG. 10 illustrates the RV kinetic energy (A), and dissipation rate (B) throughout the cardiac cycle in the PH patient (whose results are shown in solid lines) with dilated RV vs. the healthy control subject (whose results are shown in dashed lines). Three extrema for both kinetic energy and dissipation rate were found at peak systole, peak E-wave, and peak A-wave. FIG. 10 also shows streamlines of blood flow during early diastole are shown in PH (C) versus the control subject (D) determined according to embodiments of the present disclosure. FIG. 10 further shows spatial maps of the dissipation rate during peak E-wave over the RV volume of healthy control overlaid on the echo images obtained at RV focused 4Chamber view determined according to embodiments of the present disclosure. FIG. 11 shows blood flow velocity streamlines in the normal RV of the healthy control subject throughout the cardiac cycle determined according to embodiments of the present disclosure.

Figure 12:
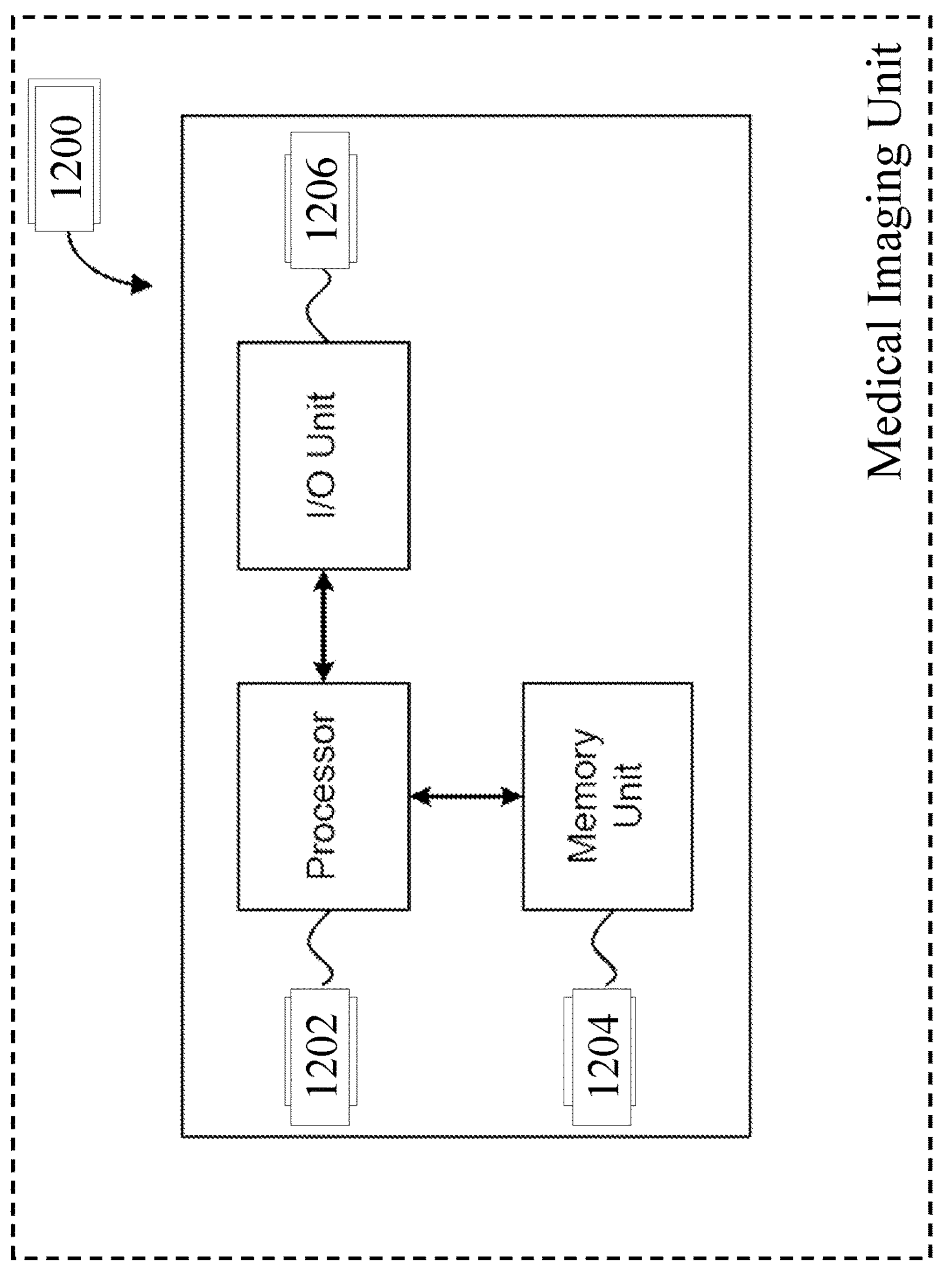
FIG. 12 illustrates a block diagram of an example device that can be configured to implement embodiments of the disclosed technology.

FIG. 12 shows a block diagram of an example embodiment of a device (or apparatus, hardware device or implementation) 1200 that implements the disclosed technology. The device includes a processor 1202 in communication with a memory unit 1204 and an input/output (I/O) unit 1206. The processor 1202 is configured to process data, and the memory unit 1204 is in communication with the processor to store and/or buffer the data. To support various functions of the device, the processor can be included to interface with and control operations of other devices, e.g., via the I/O unit 1206.

In some embodiments, and in the context of embodiments of the present technology, the processor 1202 can be configured to implement all or a portion of the correction methods described herein, and the I/O unit 1206 may be configured to receive the echo-PIV image and visualize the improved image.

In various implementations, the processor 1202 can include one or more processors, e.g., including but not limited to microprocessors such as a central processing unit (CPU), microcontrollers, or the like. The memory unit 1204 can include and store processor-executable code, which when executed by the processor, configures the device to perform various operations, e.g., such as receiving information, commands, and/or data, processing information and data, and transmitting or providing information/data to another device. The memory unit can store other information and data, such as instructions, software, values, images, and other data processed or referenced by processor. For example, various types of Random Access Memory (RAM) devices, Read Only Memory (ROM) devices, Flash Memory devices, and other suitable storage media can be used to implement storage functions of memory unit. In some implementations, the device includes an input/output unit (I/O) 1206 to interface the processor and/or memory unit to other modules, units or devices associated with the system, and/or external devices. For example, the I/O unit can connect to an external interface, source of data storage, or display device. Various types of wired or wireless interfaces compatible with typical data communication standards, such as Universal Serial Bus (USB), IEEE 1394 (FireWire), Bluetooth, Bluetooth low energy (BLE), ZigBee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE cellular communication methods, and parallel interfaces, can be used to communicate data with the device via the I/O unit. In some implementations, for example, the device 1200 includes a wireless communications unit, e.g., such as a transmitter (Tx) or a transmitter/receiver (Tx/Rx) unit. In such implementations, for example, the I/O unit can interface the processor and memory unit with the wireless communications unit to utilize various types of wireless interfaces, such as the examples described above. The I/O unit can interface with other external interfaces, sources of data storage, and/or visual or audio display devices, etc. to retrieve and transfer data and information that can be processed by the processor, stored in the memory unit, or exhibited on an output unit of a user device (e.g., display screen of a computing device) or an external device.

EXAMPLES

The following examples are illustrative of several embodiments in accordance with the present technology. Other exemplary embodiments of the present technology may be presented prior to the following listed examples, or after the following listed examples.

In some embodiments in accordance with the present technology (example A1), a method of producing velocity data associated with three-dimensional (3D) flow field images, including receiving, at one or more processors, data associated with a plurality of frames of a flow field relating to image data acquired by a medical imaging device, the data including information corresponding to measurements of the flow field over time within a chamber; performing, using the one or more processors, for each of the plurality of frames, the following operations including: generating, for a respective frame, a data correction based on an interaction of the flow field with the chamber, applying the data correction to a velocity field corresponding to the respective frame, and imposing an incompressibility constraint for the flow field on one or more data points of the respective frame; and generating, using the one or more processors, subsequent to imposing the incompressibility constraint, a plurality of corrected velocity fields each of which corresponds to one of the plurality of frames.

- Example A2 includes the method of any one or more of examples herein, in which the generating, for a respective frame, the data correction based on the interaction of the flow field with the chamber includes at least one of: generating the data correction based on the interaction of the flow field with one or more boundaries of the chamber; generating the data correction based on a two-dimensional perpendicular flow field data within the chamber; or generating the data correction based on a Doppler effect of the flow within the chamber.
- Example A3 includes the method of any one or more of examples herein, in which the data correction is based on determining a velocity of the flow field as a time derivative of a position on the one or more boundaries of the chamber that is interacting with the flow field.
- Example A4 includes the method of any one or more of examples herein, in which the image data is generated using a transducer operably coupled to the medical imaging device, and a direction of movement of the flow field is substantially similar to a direction of movement of the transducer.
- Example A5 includes the method of any one or more of examples herein, in which a portion of the image data that relates to each of the plurality of frames includes a representation limited to the chamber.
- Example A6 includes the method of any one or more of examples herein, in which the method further including: setting a sector size and an imaging depth of the medical imaging device; and acquiring image data associated with a respective frame by scanning the chamber according to the sector size and the imaging depth using the imaging device.
- Example A7 includes the method of any one or more of examples herein, in which the chamber undergoes a cyclic motion while the image data is acquired, and the receiving the data associated with the plurality of frames includes: stitching information acquired in multiple cycles of the cyclic motion of the chamber.
- Example A8 includes the method of any one or more of examples herein, in which: the chamber is a heart chamber, the cyclic motion is a cardiac motion of the heart according to a sinus rhythm, and the stitching the information acquired in multiple cycles of the cyclic motion of the chamber includes merging the information acquired in multiple cycles of cardiac motion based on the sinus rhythm.
- Example A9 includes the method of any one or more of examples herein, in which the chamber is a right ventricle of a heart.
- Example A10 includes the method of any one or more of examples herein, in which: the imaging device is an ultrasound scanner, and the data associated with the plurality of frames is acquired using a matrix probe.
- Example A11 includes the method of any one or more of examples herein, in which the data associated with the plurality of frames are determined based on a velocimetry algorithm.
- Example A12 includes the method of any one or more of examples herein, in which the velocimetry algorithm is at least one of a particle image velocimetry (PIV) algorithm, a particle tracking algorithm, a phase contrast magnetic resonance imaging (MRI) algorithm, an ultrasound velocimetry algorithm, or a multi-angular Doppler algorithm.
- Example A13 includes the method of any one or more of examples herein, in which the data associated with the plurality of frames are acquired using a contrast agent configured to be imaged as bubbles using the imaging device, and the method further includes: for each of the plurality of frames, determining a velocity field corresponding to the respective frame by tracing individual bubbles in the frame relative to at least one of an earlier frame immediately preceding the frame or a subsequent frame immediately following the frame.
- Example A14 includes the method of any one or more of examples herein, in which the incompressibility constraint is imposed by adding an irrotational field based on a solution of a Poisson equation.
- Example A15 includes the method of any one or more of examples herein, in which the Poisson equation is solved iteratively.
- Example A16 includes the method of any one or more of examples herein, in which the incompressibility constraint is imposed based on a velocity of the flow field at one or more boundaries of the chamber, at least one inlet, or at least one outlet of the chamber.

Example A17 includes the method of any one or more of examples herein, in which the method further includes monitoring, using the one or more processors, an intra-cycle variation of a parameter of the flow field based on the plurality of corrected velocity fields, wherein the intra-cycle variation of the parameter relates to a pathological condition.

Example A18 includes the method of any one or more of examples herein, in which the chamber is a right ventricle of a heart, the parameter of the flow field being monitored includes a vortex, a flow kinetic energy, or a dissipation rate per cardiac cycle, and the method further includes: predicting whether the pathological condition exists based on the intra-cycle variation of the parameter.

Example A19 includes the method of any one or more of examples herein, in which the predicting whether the pathological condition exists includes: comparing the intra-cycle variation of the parameter with a reference intra-cycle variation of the parameter; determining that a difference between the intra-cycle variation of the parameter with a reference intra-cycle variation of the parameter exceeds a threshold; and in response to determining that the difference between the intra-cycle variation of the parameter with a reference intra-cycle variation of the parameter exceeds a threshold, determining that the pathological condition exists.

B1. A method to predict the flow velocities through, within and off of a chamber based on knowledge of the positions of a set of points that are distributed over the surface of a chamber with inlets and outlets whose positions change in spatial dimensions and in time.

B2. The method in solution B1 in which at the chamber boundaries, the velocity of the flow is calculated as the time derivative of the positions of the point over the surface of the chamber given that the volume of the chamber by considering the spatial distribution of the points on the surface of the chamber. At the chamber's inlets and outlets, the velocity is calculated by imposing the conservation of the mass principle as the rate of volumetric changes per area of the inlet or outlet.

B3. Inlet or outlet velocity calculated as in solution B2 where it is corrected by the velocity of chamber boundaries.

B4. Considering that the 3D flow velocity inside the chamber is measured or computationally calculated by an independent velocimetry method, the flow velocity at the boundary, inlets and outlets shall be equal to the velocity of the boundaries as measured in solutions B1 to B3. If not, in our method the flow velocity at the boundaries, inlets and outlets will be replaced by its value measured as in solutions B1 to B3.

B5. Imposing the incompressibility constraint to the whole flow velocity field inside the chamber while keeping the velocity values at the chamber's boundaries, inlets, and outlets (as in solutions B1 to B3), leads to correction of the flow velocity field independently measured or calculated.

B6. The method in solution B5 in which the incompressibility is imposed the correction to the flow velocity field such that the correction includes the velocities at the chamber's boundaries, inlets, and outlets.

B7. The flow velocimetry methods described in solution B4 are such as but not limited to particle image velocimetry, particle tracking method, phase contrast MRI (e.g., 4D Flow MRI), ultrasound velocimetry, multiangular Doppler.

B8. The methods in solution B5 or B6 in which the incompressibility constraint is applied by adding an irrotational field such as the one obtained based on the solution of the Poisson Equation.

B9. The method in solution B8 in which the Poisson Equation is solved iteratively.

B10. The method in solution B9 in which an approximate solution is obtained after few iterations less than infinity.

B11. The method as in solutions B1 to B10 such that the chamber is a heart chamber.

In some embodiments, a method of producing velocity data associated with three-dimensional (3D) flow field images, comprises receiving, from a medical imaging device, data associated with a plurality of frames comprising information corresponding to measurements of a flow field within a chamber, performing, for each of the plurality of frames, the following operations generating, for a respective frame, a data correction based on an interaction of the flow fields with one or more boundaries of the chamber, applying the data correction to the respective velocity field, and imposing an incompressibility constraint for the flow field on one or more data points of the respective frame, and generating, subsequent to imposing the incompressibility constraint, a plurality of corrected velocity fields.

In these embodiments, the data correction is based on determining a velocity of the flow field as a time derivative of a position on the one or more boundaries of the chamber that is interacting with the flow field.

In some embodiments, a method of producing image-based velocity data associated with three-dimensional (3D) flow field images, comprises receiving, from a medical imaging device, a plurality of frames comprising information corresponding to measurements of a flow field within a chamber, performing, for each of the plurality of frames, the following operations generating, for a respective frame, a data correction based on a two-dimensional perpendicular flow field data within the chamber, applying the data correction to the respective velocity field, and imposing an incompressibility constraint for the flow field on one or more data points of the respective frame, and generating, subsequent to imposing the incompressibility constraint, a plurality of corrected velocity fields.

In some embodiments, a method of producing image-based velocity data associated with three-dimensional (3D) flow field images comprises receiving, from a medical imaging device, a plurality of frames comprising information corresponding to measurements of a flow field within a chamber, performing, for each of the plurality of frames, the following operations generating, for a respective frame, a data correction based on a Doppler effect of the flow within the chamber, applying the data correction to the respective velocity field, and imposing an incompressibility constraint for the flow field on one or more data points of the respective frame, and generating, subsequent to imposing the incompressibility constraint, a plurality of corrected velocity fields.

In these embodiments, the image-based velocity data associated with the 3D flow field images is generated using a transducer, and wherein a direction of movement of the flow field is substantially similar to a direction of movement of the transducer.

In the embodiments described above, the 3D flow field image-based data are calculated based on a velocimetry method. For example, the velocimetry method is at least one of a particle image velocimetry (PIV) method, a particle tracking method, a phase contrast magnetic resonance imaging (MRI) method, an ultrasound velocimetry method, or a multi-angular Doppler method.

In the embodiments described above, the incompressibility constraint is imposed by adding an irrotational field based on a solution of a Poisson equation, which is solved iteratively.

In the embodiments described above, the incompressibility constraint is imposed based on a velocity of the flow field at the one or more boundaries, at least one inlet, or at least one outlet of the chamber.

In the embodiments described above, the chamber is a heart chamber.

Various embodiments of the present document relate to systems and/or devices configured to execute the methods of any one or more of examples herein, and non-transitory computer-readable media storing instructions, that when executed by one or more processors, effectuate the methods of any one or more of examples herein.

It is understood that the various disclosed embodiments may be implemented individually, or collectively, in devices comprised of electronic components, hardware and/or software modules and components. These devices, for example, may comprise a processor, a memory unit, an interface that are communicatively connected to each other, and may range from desktop and/or laptop computers, to mobile devices and the like. The processor and/or controller can be in communication with at least one memory and with at least one communication unit that enables the exchange of data and information, directly or indirectly, through the communication link with other entities, devices, and networks. The communication unit may provide wired and/or wireless communication capabilities in accordance with one or more communication protocols, and therefore it may comprise the proper transmitter/receiver antennas, circuitry, and ports, as well as the encoding/decoding capabilities that may be necessary for proper transmission and/or reception of data and other information.

Various information and data processing operations described herein may be implemented in one embodiment by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), etc. Therefore, the computer-readable media that is described in the present application comprises non-transitory storage media. Generally, program modules may include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described, and other implementations, enhancements and variations can be made based on what is described and illustrated in this patent document.

What is claimed is:

1. A method of producing velocity data associated with three- dimensional (3D) flow field images, comprising:

receiving, at one or more processors, data associated with a plurality of frames of a flow field relating to image data acquired by a medical imaging device, the data comprising information corresponding to measurements of the flow field over time within a chamber;

performing, using the one or more processors, for each of the plurality of frames, the following operations including:

generating, for a respective frame, a data correction based on an interaction of the flow field with the chamber, wherein generating the data correction comprises at least one of:

generating the data correction based on the interaction of the flow field with one or more boundaries of the chamber, wherein the data correction is based on determining a velocity of the flow field as a time derivative of a position on the one or more boundaries of the chamber that is interacting with the flow field, generating the data correction based on a two-dimensional perpendicular flow field data within the chamber, or generating the data correction based on a Doppler effect of the flow field within the chamber, applying the data correction to a velocity field corresponding to the respective frame, and imposing an incompressibility constraint for the flow field on one or more data points of the respective frame; and generating, using the one or more processors, subsequent to imposing the incompressibility constraint, a plurality of corrected velocity fields each of which corresponds to one of the plurality of frames.

2. The method of claim 1 wherein:

the image data is generated using a transducer operably coupled to the medical imaging device, and a direction of movement of the flow field is substantially similar to a direction of movement of the transducer.

3. The method of claim 1, wherein a portion of the image data that relates to each of the plurality of frames comprises a representation limited to the chamber.

4. The method of claim 3, further comprising:
setting a sector size and an imaging depth of the medical imaging device; and
acquiring image data associated with a respective frame by scanning the chamber according to the sector size and the imaging depth using the medical imaging device.

5. The method of claim 1, wherein:
the chamber undergoes a cyclic motion while the image data is acquired, and
the receiving the data associated with the plurality of frames comprises:
stitching information acquired in multiple cycles of the cyclic motion of the chamber.

6. The method of claim 5, wherein:
the chamber is a chamberof a heart,
the cyclic motion is a cardiac motion of the heart according to a sinus rhythm, and
the stitching the information acquired in the multiple cycles of the cyclic motion of the chamber comprises merging the information acquired in the multiple cycles of the cardiac motion based on the sinus rhythm.

7. The method of claim 6, wherein the chamber is a right ventricle of a heart.

8. The method of claim 1, wherein:
the medical imaging device is an ultrasound scanner, and
the data associated with the plurality of frames is acquired using a matrix probe.

9. The method of claim 1, wherein the data associated with the plurality of frames are determined based on a velocimetry algorithm.

10. The method of claim 9, wherein the velocimetry algorithm is at least one of a particle image velocimetry (PIV) algorithm, a particle tracking algorithm, a phase contrast magnetic resonance imaging (MRI) algorithm, an ultrasound velocimetry algorithm, or a multi- angular Doppler algorithm.

11. The method of claim 9, wherein:
the data associated with the plurality of frames are acquired using a contrast agent configured to be imaged as bubbles using the medical imaging device, and
the method further comprises:
for each of the plurality of frames, determining the velocity field corresponding to the respective frame by tracing individual bubbles in a frame relative to at least one of an earlier frame immediately preceding the frame or a subsequent frame immediately following the frame.

12. The method of claim 1, wherein the incompressibility constraint is imposed by adding an irrotational field based on a solution of a Poisson equation.

13. The method of claim 12, wherein the Poisson equation is solved iteratively.

14. The method of claim 1, wherein the incompressibility constraint is imposed based on the velocity of the flow field at the one or more boundaries of the chamber, at least one inlet, or at least one outlet of the chamber.

15. The method of claim 1, further comprising:
monitoring, using the one or more processors, an intra-cycle variation of a parameter of the flow field based on the plurality of corrected velocity fields, wherein the intra-cycle variation of the parameter relates to a pathological condition.

16. The method of claim 15, wherein:
the chamber is a right ventricle of a heart,
the parameter of the flow field being monitored comprises a vortex, a flow kinetic energy, or a dissipation rate per cardiac cycle, and
the method further comprises: predicting whether the pathological condition exists based on the intra-cycle variation of the parameter.

17. A system for producing velocity data associated with three- dimensional (3D) flow field images, comprising: a processor configured to perform operations including:
receiving data associated with a plurality of frames of a flow field acquired by a medical imaging device, the data comprising information corresponding to measurements of the flow field over time within a chamber;
performing for each of the plurality of frames, operations including:
generating, for a respective frame, a data correction based on an interaction of the flow field with the chamber, wherein generating the data correction comprises at least one of:
generating the data correction based on the interaction of the flow field with one or more boundaries of the chamber, wherein the data correction is based on determining a velocity of the flow field as a time derivative of a position on the one or more boundaries of the chamber that is interacting with the flow field,
generating the data correction based on a two-dimensional perpendicular flow field data within the chamber, or
generating the data correction based on a Doppler effect of the flow field within the chamber,
applying the data correction to a velocity field corresponding to the respective frame, and
imposing an incompressibility constraint for the flow field on one or more data points of the respective frame; and
generating subsequent to imposing the incompressibility constraint, a plurality of corrected velocity fields each of which corresponds to one of the plurality of frames.

18. One or more non-transitory computer readable media storing computer program instructions that, when executed by one or more processors, effectuate operations comprising:
receiving data associated with a plurality of frames of a flow field acquired by a medical imaging device, the data comprising information corresponding to measurements of the flow field over time within a chamber;
performing for each of the plurality of frames, operations including:
generating, for a respective frame, a data correction based on an interaction of the flow field with the chamber, wherein generating the data correction comprises at least one of:
generating the data correction based on the interaction of the flow field with one or more boundaries of the chamber, wherein the data correction is based on determining a velocity of the flow field as a time derivative of a position on the one or more boundaries of the chamber that is interacting with the flow field,
generating the data correction based on a two-dimensional perpendicular flow field data within the chamber, or
generating the data correction based on a Doppler effect of the flow field within the chamber,
applying the data correction to a velocity field corresponding to the respective frame, and imposing an incompressibility constraint for the flow field on one or more data points of the respective frame; and generating, subsequent to imposing the incompressibility constraint, a plurality of corrected velocity fields each of which corresponds to one of the plurality of frames.

* * * * *